US00PP15624P3

(12) United States Plant Patent

Yokoi

(10) Patent No.: US PP15,624 P3
(45) Date of Patent: Mar. 8, 2005

(54) *HYDRANGEA PANICULATA* PLANT NAMED 'SHIKOKU FLASH'

(50) Latin Name: *Hydrangea paniculata*
Varietal Denomination: Shikoku flash

(75) Inventor: Masato Yokoi, Kawaguchi (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/736,758

(22) Filed: Dec. 12, 2000

(65) Prior Publication Data

US 2002/0073454 P1 Jun. 13, 2002

(51) Int. Cl.[7] ..... A01H 5/00

(52) U.S. Cl. ..... Plt./250

(58) Field of Search ..... Plt./250

(56) References Cited

U.S. PATENT DOCUMENTS

PP10,751 P * 1/1999 De Belder ..... Plt./250

* cited by examiner

*Primary Examiner*—Kent L. Bell
(74) *Attorney, Agent, or Firm*—Christie, Parker & Hale, LLP

(57) ABSTRACT

A new plant variety of *Hydrangea paniculata* named 'Shikoku Flash' having clear white mottled foliage growth throughout the growing season.

1 Drawing Sheet

BOTANICAL CLASSIFICATION

Figure 1:
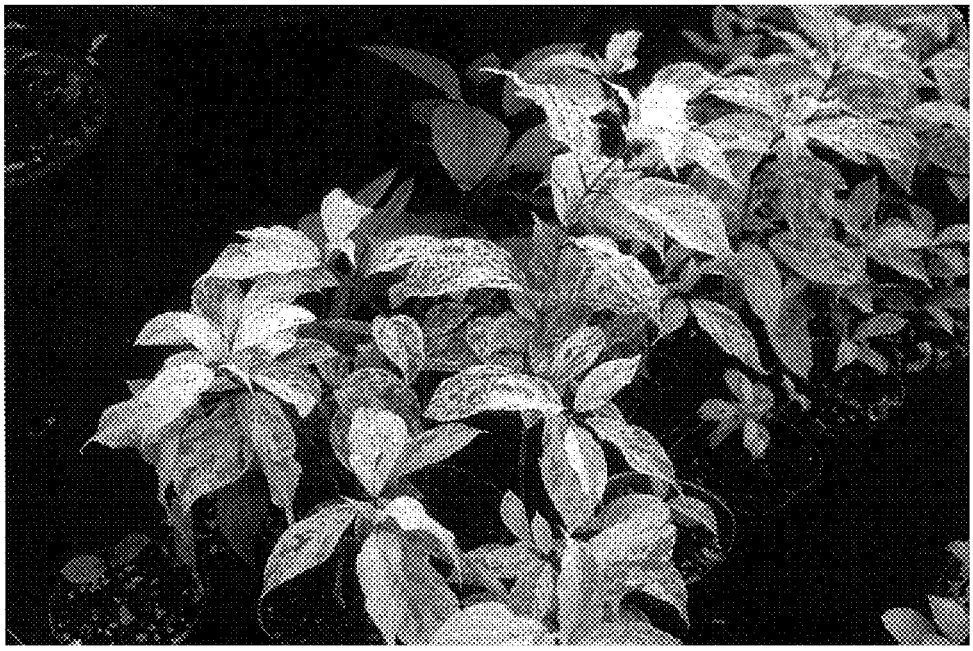

*Hydrangea paniculata* Sieb.

VARIETY DENOMINATION

'Shikoku Flash'.

BACKGROUND OF THE INVENTION

The present invention relates to a new and distinct variety of *Hydrangea paniculata* Sieb., which was discovered as a chance seedling in a controlled planting of *Hydrangea paniculata* (unnamed) (unpatented) by the inventor, Dr. Masato Yokoi, in Ehime Prefecture, Shikoku, Japan. The varietal denomination of the new variety is 'SHIKOKU FLASH'.

The genus *Hydrangea* is included in the family Saxifragaceae which comprises about 80 genera and 1,200 species of herbs, shrubs, small trees, and woody climbers mostly temperate in origin. *Hydrangea* comprises approximately 23 species of deciduous or evergreen shrubs and vines originating in North America, South America and East Asia, many of which possess desirable ornamental characteristics. Recent taxonomical treatments sometimes isolate *Hydrangea* in a new family, Hydrangeaaceae.

*Hydrangea paniculata* is widespread and common throughout much of Japan and eastern and southern China. It generally has opposite, occasionally whorled, simple leaves, elliptic or ovate in shape with acuminate apex, 5 to 15 cm long and 5 to 10 cm wide. Leaves are generally softly pubescent. Leaf color ranges from light to dark green, depending on light intensity and cultural conditions. The plant is deciduous. Flower color is white, often changing to pink as the season progresses.

Flowers of *Hydrangea paniculata* are borne in mostly conical or pyramidal panicles 15 to 20 cm long with a few white to pink sterile flowers each 1.75 to 3 cm wide. Fertile flowers are numerous, blooming in summer and early fall.

SUMMARY OF THE INVENTION

The new variety was discovered as a chance seedling in a controlled planting of *Hydrangea paniculata* (unnamed) (unpatented). Asexual reproduction of the new variety by stem cuttings performed in Saitama Prefecture, Japan and Lewisberry, Pa. have confirmed that the distinctive characteristics of the new variety are stable and transmitted to succeeding generations.

COMPARISON

'SHIKOKU FLASH' is distinguished from plants of the unnamed, unpatented, *Hydrangea paniculata* and all other varieties of *Hydrangea paniculata* known to the inventor by the pigmentation of the leaves, which exhibit mottled clear white variegated foliage throughout the growing season.

BRIEF DESCRIPTION OF THE ILLUSTRATION

The accompanying photographic illustration shows a specimen of the new cultivar as true to color as is reasonably possible to make in an illustration of this character.

In the illustration:

FIG. 1 illustrates the distinctive mottled, clear white variegated foliage.

DETAILED DESCRIPTION OF THE NEW VARIETY

'SHIKOKU FLASH' has not been observed under all possible environmental, cultural, and light conditions. The following observations and descriptions are of 5-year-old plants grown in 5-gallon containers at Lewisberry, Pa. and Saitama Prefecture, Japan. Phenotypic expression may vary with light intensity and cultural and environmental conditions. In this description, color references are to The Royal Horticultural Society Colour Chart (1995), and terminology used in the color descriptions herein refers to plate numbers in this color chart.

Classification:

*Botanical.*—*Hydrangea paniculata* Sieb. 'SHIKOKU FLASH'.

*Parentage.*—A chance seedling in a controlled planting of *Hydrangea paniculata* (unnamed) (unpatented).

*Propagation.*—By vegetative cuttings.

Plant:

*Size.*—Mature plant can grow to a height of 3 to 5 m.

*Branching.*—Opposite branched.

*Habit.*—Upright, mound forming deciduous shrub.

*Leaf shape.*—Ovate; acuminate apex; attenuate base.

*Leaf margin.*—Serrate.

*Leaf texture.*—Thick; pubescent to nearly glabrous on top; setose pubescent on bottom, especially on veins.

*Leaf color.*—Color varies with intensity of sunlight and cultural conditions (see below). Background color is generally yellow early in the growing season tending toward chartreuse as the foliage ages; mottled white variegation covers 80% to 90% of typical mature leaf. Adaxial: Clear white variegation near White Group 155D; medium green background near Green Group 141B. Abaxial: Clear white variegation near White Group 155D; medium green background near Green Group 143D.

*Stems.*—Length: To 1 m long. Diameter: 1 cm at the base. Color: Near Grey-Brown Group 199D at base.

*Internodes.*—3 cm average.

*Petioles.*—Size: 2.5 cm long. Color: Near Red Group 53C.

*Leaf size.*—Up to approximately 15 cm long and 8 cm wide.

*Texture and substance.*—Flat, dull in appearance.

*Hardiness.*—USDA Zone 3 (−40° F. to −30° F.).

*Pests/diseases.*—No pest or disease problems noted.

Inflorescence:

*Bloom period.*—Late summer until fall.

*Lastingness of individual bloom.*—Approximately 4 weeks on the plant.

*Inflorescence form.*—Paniculate, upright conical.

*Inflorescence arrangement.*—Panicles; conical to pyramidal.

*Number of panicles.*—Observed plants exhibited 5 panicles. Length of panicle: 15 to 20 cms. Width of panicle: 5 to 8 cms.

*Inflorescence size.*—About 1 to 2 cm long, 1.75 to 3 cm across. Fertile flowers are numerous, more than 100.

*Color.*—Clear white, near White Group 155D.

*Shape of inflorescence.*—Conical.

*Fragrance.*—None noted.

Reproductive organs:

*Stamens.*—4 to 5.

*Stigma.*—1.

*Pistil.*—1.

*Fruit.*—Extremely small, dust-like; near Brown Group 200B.

Sepalous florets:

*Number of sepals.*—4 to 5.

*Aspect of sepals.*—Flat, occasionally slightly incurved.

*Size of sepals.*—Approximately 75 mm wide.

*Shape.*—Oval. Apex: Retuse. Base: Attenuate.

*Margin.*—Entire.

*Color.*—Top: Near White Group 155D. Bottom: Near White Group 155D.

I claim:

1. A new variety of *Hydrangea paniculata* plant, as illustrated and described.

* * * * *